US008198585B2

(12) United States Patent
Yamaguchi

(10) Patent No.: US 8,198,585 B2
(45) Date of Patent: Jun. 12, 2012

(54) CHROMATOGRAPH MASS SPECTROMETER

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 594 days.

(21) Appl. No.: 12/166,707

(22) Filed: Jul. 2, 2008

(65) Prior Publication Data

US 2009/0008548 A1 Jan. 8, 2009

(30) Foreign Application Priority Data

Jul. 3, 2007 (JP) ................................ 2007-174768

(51) Int. Cl.
*H01J 49/26* (2006.01)

(52) U.S. Cl. ........ 250/288; 250/281; 250/282; 250/286; 250/287; 702/19; 702/23; 702/27; 702/30; 702/31

(58) Field of Classification Search .................. 250/281, 250/282, 286, 287, 288; 702/19, 23, 24, 702/26, 27, 30, 31, 32
See application file for complete search history.

(56) References Cited

U.S. PATENT DOCUMENTS

| 4,353,242 | A | * | 10/1982 | Harris et al. ................. 73/23.36 |
| 5,969,228 | A | * | 10/1999 | Gorenstein .................. 73/23.22 |
| 7,373,256 | B2 | * | 5/2008 | Nicholson et al. ............. 702/19 |
| 7,433,787 | B2 | * | 10/2008 | Barrett et al. .................. 702/22 |
| 7,473,892 | B2 | * | 1/2009 | Sano et al. .................... 250/281 |
| 7,691,643 | B2 | * | 4/2010 | Yamashita et al. ............ 436/173 |
| 7,693,899 | B2 | * | 4/2010 | Ireland et al. ................. 707/713 |
| 7,873,481 | B2 | * | 1/2011 | Walk et al. ..................... 702/19 |
| 2005/0127287 | A1 | * | 6/2005 | Plumb et al. ................. 250/281 |

(Continued)

FOREIGN PATENT DOCUMENTS

| JP | 2001-165922 A | 6/2001 |
| JP | 2001-249114 A | 9/2001 |
| JP | 2007-017218 A | 1/2007 |
| JP | 2007-147464 A | 6/2007 |

OTHER PUBLICATIONS

"LCMS-IT-TOF," Shimadzu North America, Internet <http://www.ssi.shimadzu.com/products.cfm?product=lcms_it_tof>, Apr. 15, 2008, Accessed Jun. 18, 2008.

(Continued)

*Primary Examiner* — Phillip A Johnston
*Assistant Examiner* — Michael Logie
(74) *Attorney, Agent, or Firm* — Sughrue Mion, PLLC

(57) ABSTRACT

A chromatograph mass spectrometer is provided for obtaining the information pertinent to a structural analysis, with a simple operation, on a compound series including a plurality of compounds whose structures and characters are similar. First, based on the data obtained by a normal LC/MS analysis, a two-dimensional isointensity line graph is created and displayed with a retention time and a mass-to-charge ratio on the two axes and with a signal intensity represented in contour (S1 and S2). When the operator specifies a desired range by a drag operation or the like by a mouse (S3), peaks included in the range specified are extracted and based on the peaks, precursor ions are selected (S4 through S6). Then a schedule is created so that an $MS^2$ analysis is performed for the precursor ions selected in the course of an LC/MS analysis for the sample to be targeted (S7). Analyses are performed while properly performing the precursor ions' selection/dissociation process in accordance with the schedule to collect the $MS^2$ spectrum data (S8).

7 Claims, 3 Drawing Sheets

U.S. PATENT DOCUMENTS

| | | | | |
|---|---|---|---|---|
| 2006/0109271 A1* | 5/2006 | Lomask | ............... | 345/440 |
| 2006/0289736 A1* | 12/2006 | Yamashita et al. | ............... | 250/282 |
| 2007/0176088 A1* | 8/2007 | Li | ............... | 250/282 |
| 2008/0237457 A1* | 10/2008 | Yamashita | ............... | 250/281 |

OTHER PUBLICATIONS

Japanese Office Action dated Dec. 6, 2011, issued in corresponding Japanese Application No. 2007-174768.

* cited by examiner

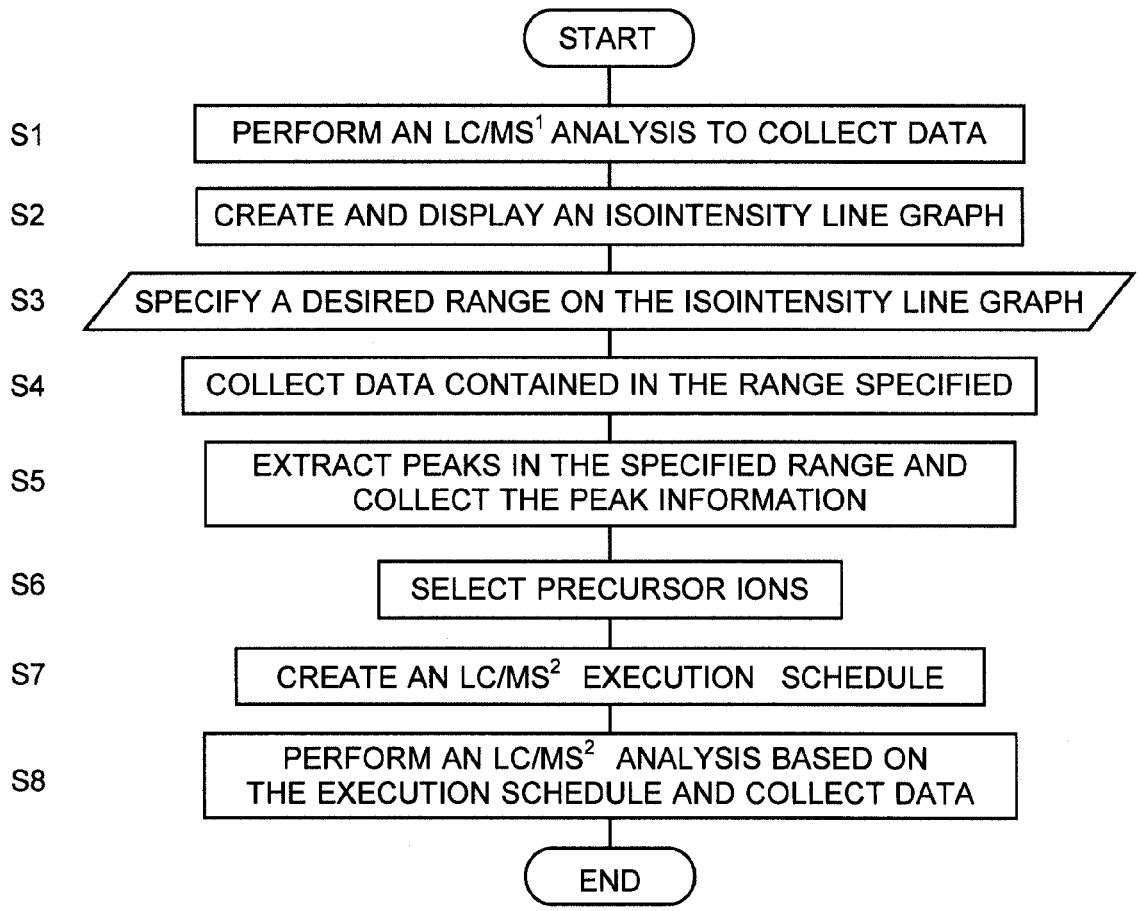
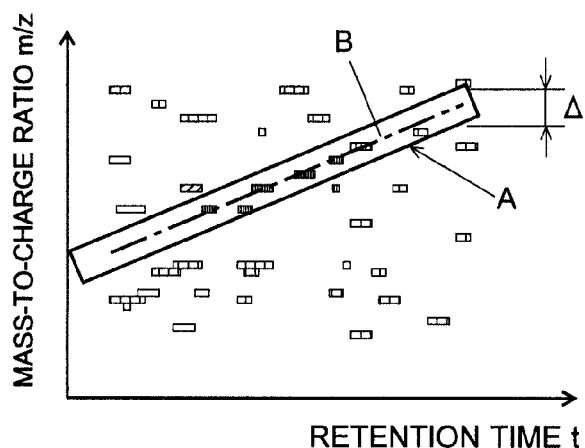

Fig. 4

| RETENTION TIME | PRECURSOR ION'S MASS |
|---|---|
| 0 ~ t1 | |
| t1 ~ t2 | m1, m2 |
| t2 ~ t3 | m4 |
| t4 ~ t5 | m4, m5, m6 |
| ⋮ | ⋮ |

CHROMATOGRAPH MASS SPECTROMETER

The present invention relates to a chromatograph mass spectrometer, such as a gas chromatograph mass spectrometer (GC/MS) or a liquid chromatograph mass spectrometer (GC/MS), in which a chromatograph for temporally separating various components included in a sample and a mass spectrometer for sequentially mass-analyzing the separated components are combined. More specifically, the present invention relates to a chromatograph mass spectrometer using a mass spectrometer capable of an $MS^n$ analysis.

BACKGROUND OF THE INVENTION

One of the well-known mass-analyzing methods for identifying a substance having large molecular weight and for analyzing its structure is an MS/MS analysis (or tandem analysis). In a general MS/MS analysis, an ion having a specific mass-to-charge ratio is first selected as a precursor ion from a variety of ions originating from a sample. Next, the precursor ion is dissociated into a variety of product ions by a CID (collision induced dissociation) process or other process. The product ions thus created are mass-analyzed to create a mass spectrum (an MS/MS spectrum or $MS^2$ spectrum) for example. Then the mass spectrum is analyzed to identify the original molecule and determine its structure. In some cases, an $MS^n$ analysis may be performed in which the following operation/analysis is repeatedly performed: a precursor ion is further selected from product ions to be dissociated and the product ions created by this operation are mass-analyzed.

Conventionally, a liquid chromatograph mass spectrometer (LC/MS) in which a mass spectrometer capable of such $MS^n$ analysis is used as a detector of a liquid chromatograph has been developed as disclosed in Non-Patent Document 1. In such an LC/MS, data having three dimensions, i.e. a retention time, mass-to-charge ratio, and signal intensity is collected. Based on the data, a mass chromatogram, mass spectrum, and total ion mass chromatogram are created. The mass chromatogram shows the relationship between the retention time and signal intensity for a specified mass-to-charge ratio, the mass spectrum shows the relationship between the mass-to-charge ratio and signal intensity for a specified retention time, and the total ion mass chromatogram shows the relationship between the retention time and signal intensity without a limitation of the mass-to-charge ratio. It is also possible, based on the data obtained from the analysis, to set an ion to be focused as a precursor ion to perform an $MS^2$ analysis for this precursor ion.

Conventionally, in selecting a precursor ion based on the data obtained from an $MS^1$ analysis, a selection reference is used such as: descending order of the signal intensity or ascending order of the mass-to-charge ratio of a plurality of peaks having a signal intensity larger than a predetermined threshold value among the peaks appearing in a mass spectrum. However, with such conventional precursor ion selection methods, an ion selected as a precursor ion is not always one originating from the component of interest in the case where many peaks appear for example.

Non-Patent Document 1: "LCMS-IT-TOF", SHIMADZU NORTH AMERICA, Internet <http://www.ssi.shimadzu.com/products/product.cfm?product=lcms_it_tof> [Apr. 15, 2008]

SUMMARY OF THE INVENTION

In the field of development/research of medical supplies and agrichemicals for example, a series of compounds having similar structures or characters is often required to be examined. Although the retention time and mass-to-charge ratio often have a specific relationship in such a compound series, conventional apparatuses are not intended for exhaustively selecting plural components included in a compound series to obtain an $MS^n$ spectrum. This requires complicated operations in performing such an analysis; hence, it has been difficult to improve the working efficiency.

The present invention is accomplished in view of such problems, and the objective thereof is to provide a chromatograph mass spectrometer capable of assuredly obtaining the accurate information with a simple operation on a specified compound series or the like.

The present invention developed to solve the aforementioned problem provides a chromatograph mass spectrometer in which a chromatograph for separating a sample into components and a mass spectrometer for mass analyzing the sample components separated by the chromatograph are combined, and the mass spectrometer being capable of an $MS^n$ analysis in which an ion having a specific mass-to-charge ratio is selected as a precursor ion, the precursor ion selected is dissociated, and product ions created through the dissociation are mass analyzed, including:

a) a graph displayer for creating a graph, based on data obtained by performing an $MS^1$ analysis, with a retention time and a mass-to-charge ratio on two axes on a plane, and with a signal intensity represented in contour or represented by an intensity-discriminable expression equivalent to the contour, and for displaying the graph on a display screen;

b) a specifier for allowing a user to specify an intended range on the graph displayed by the graph displayer;

c) a precursor ion selector for selecting one or more ions, as a precursor ion, corresponding to a peak or peaks existing in the range specified by the specifier or a remaining peak or peaks other than the peak or peaks existing in the range; and d) an analysis controller for sequentially performing a series of predetermined $MS^2$ analyses, as time progresses, for the precursor ion or ions selected by the precursor ion selector.

The "chromatograph mass spectrometer" in the present invention is typically a liquid chromatograph mass spectrometer or a gas chromatograph mass spectrometer. The mass spectrometer may be any type as long as it is able to perform an $MS^n$ analysis. The means for selecting an ion having a specific mass-to-charge ratio and dissociating it may be, but not limited to, a three-dimensional quadrupole ion trap, linear ion trap, or other types of units. The means for mass separating a general ion or product ion may be, but not limited to, a quadrupole mass filter, time-of-flight mass analyzer or other types of units.

In the chromatograph mass spectrometer according to the present invention, the sample to be targeted in an $MS^1$ analysis and the sample to be targeted in an $MS^2$ analysis performed under the control of the analysis controller may be identical; however, they may not necessarily be the same sample. For example, a standard sample (or a known sample) containing a component which is supposed to be contained in a target sample may be a target to be analyzed in an $MS^1$ analysis, and the target sample (or an unknown sample) may be a target to be analyzed in an $MS^2$ analysis. Specifically, such a sample including plural components may be analyzed in an $MS^1$ analysis in the case where an $MS^2$ spectrum for plural components included in a certain compound series and having similar structures is required.

The aforementioned graph "with a retention time and a mass-to-charge ratio on two axes on a plane" may be of any form as long as it can express three dimensions: retention time, mass-to-charge ratio and signal intensity. An example of such graphs is a "two-dimensional contour graph" drawn on a plane with the aforementioned two axes intersecting each other at right angles and contour lines representing the signal intensity; another example is a "three-dimensional contour graph" in which the altitude of a signal intensity is viewed from a diagonal direction.

In the chromatograph mass spectrometer according to the present invention, the specifier may allow the user to set a frame having a certain form and size on a displayed graph through a drag or similar operation using a pointing device (such as a mouse), so that the range surrounded by the frame is specified as the aforementioned range. In the case where it is known in advance that the range to be seen on the graph can be approximately represented by an expression such as a primary expression, it is possible to allow the user to enter that expression and a margin value (this may be a default value) expressing the deviation from the expression, to set the aforementioned range based on it.

When a certain range is specified by the specifier, the precursor ion selector collects information, e.g. a mass-to-charge ratio and retention time, on peaks existing in the range specified for example, and determines the ions corresponding to the peaks to be precursor ions. At this point, it is not necessary to select all the peaks existing in the range specified. The peaks may be chosen in accordance with other conditions; for example, a peak or peaks having larger signal intensity than a predetermined threshold value may be selectively chosen to determine a precursor ion. After the selection of precursor ions, the analysis controller performs an $MS^2$ analysis for the precursor ion selected from the sample whose components have been separated by a chromatograph. Specifically, the analysis controller performs a mass selection of ions, a dissociation operation of the selected ion having a specific mass-to-charge ratio, and a mass analysis of the product ions created by the dissociation operation.

With the chromatograph mass spectrometer according to the present invention, when the user specifies an appropriate range in a graph so that the range includes one compound series in which a mass-to-charge ratio and a retention time show a specific relationship for example, $MS''$ spectrum data in which ions originating from a plurality of components included in the compound series serve as precursor ions can be collected. Therefore, ions corresponding to the peaks which are neither pertinent nor necessary are not selected as precursor ions. Even in the case where the signal intensity of ions originating from a certain compound included in a compound series to be focused is relatively small, it is possible to assuredly obtain an $MS''$ spectrum in which the ions are set as precursor ions. Accordingly, it is possible to obtain, with a very simple operation, the useful information on a structural analysis for the plural compounds belonging to a compound series.

BRIEF DESCRIPTION OF THE DRAWINGS

FIG. 2 is a flowchart illustrating the procedure of the characteristic analysis operation in the LC/MS according to the present embodiment.

FIG. 3 is a diagram illustrating an example of an isointensity line graph displayed on the screen of the display unit of the LC/MS according to the present embodiment.

FIG. 4 is a diagram illustrating an example of an $LC/MS^2$ execution schedule created in the LC/MS according to the present embodiment.

EXPLANATION OF THE NUMERALS

Figure 1:
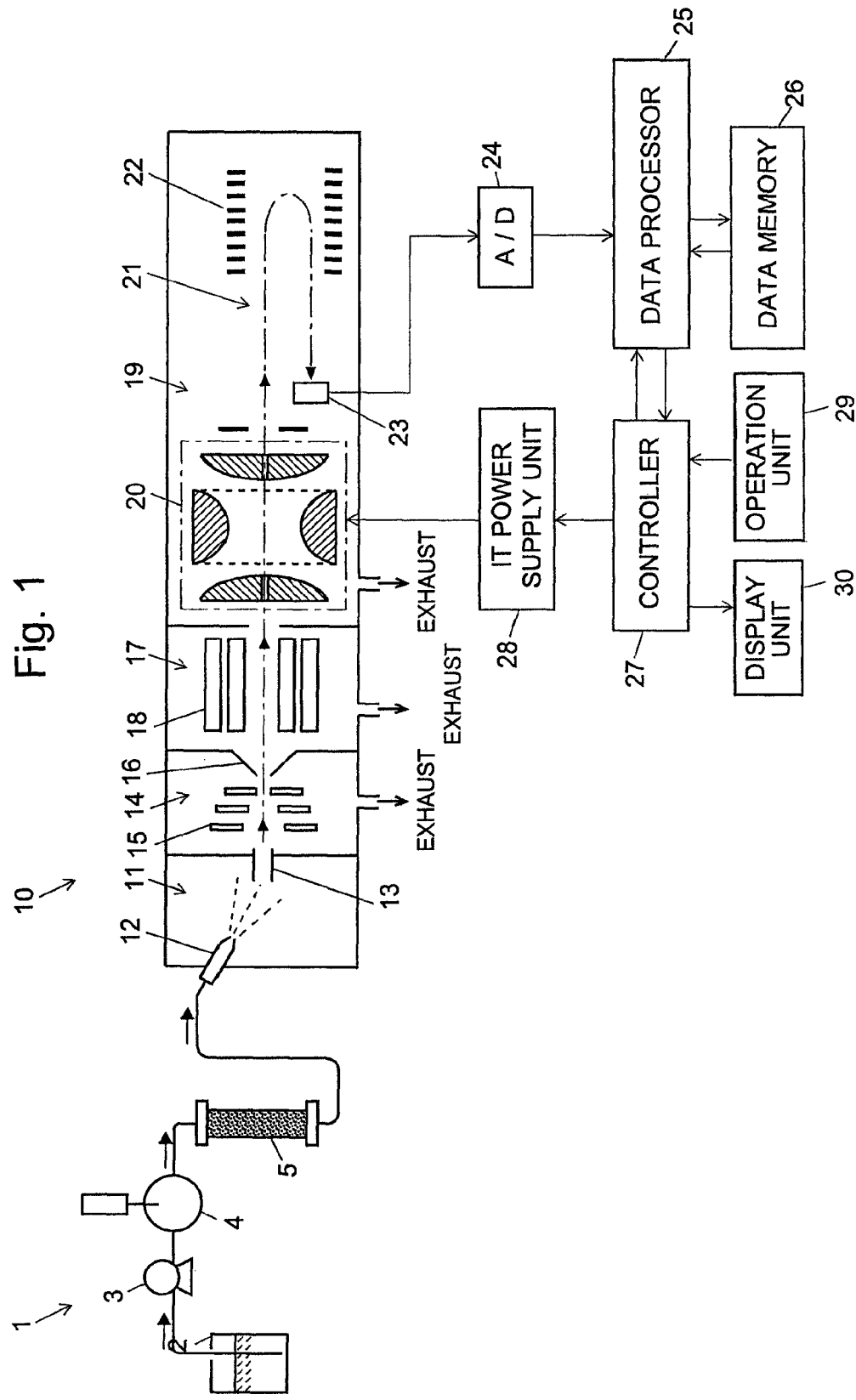
FIG. 1 is a schematic configuration diagram of an LC/MS according to an embodiment of the present invention.

1 . . . Liquid Chromatograph
2 . . . Mobile Phase Container
3 . . . Liquid Sending Pump
4 . . . Injector
5 . . . Column
10 . . . Mass Spectrometer
11 . . . Ionization Chamber
12 . . . Electrospray Nozzle
13 . . . Heating Pipe
14 . . . First Intermediate Vacuum Chamber
15 . . . First Ion Lens
16 . . . Skimmer
17 . . . Second Intermediate Vacuum Chamber
18 . . . Second Ion Lens
19 . . . Analysis Chamber
20 . . . Ion Trap
21 . . . Time-Of-Flight Mass Separator
22 . . . Reflectron
23 . . . Ion Detector
24 . . . A/D Converter
25 . . . Data Processor
26 . . . Data Memory
27 . . . Controller
28 . . . IT Power Supply Unit
29 . . . Operation Unit
30 . . . Display Unit

DETAILED DESCRIPTION OF A PREFERRED EMBODIMENT

Hereinafter, an explanation will be made, with reference to figures, for an LC/MS which is an embodiment of the chromatograph mass spectrometer according to the present invention. FIG. 1 is a schematic configuration diagram of an LC/MS according to the present embodiment.

In the liquid chromatograph 1, a mobile phase held in a mobile phase container 2 is siphoned at an approximately constant flow rate by a liquid sending pump 3 to be provided to a column 5. The sample to be analyzed is introduced to the mobile phase from an injector 4 at a predetermined timing. The sample on the mobile phase is sent into the column 5. While passing through the column 5, various components included in the sample are temporally separated to be eluted from the column 5 in series. The sample liquid including these eluted sample components is introduced to the mass spectrometer 10.

The sample liquid is sprayed into the ionization chamber 11 at an atmosphere of approximate atmospheric pressure from the electrospray nozzle 12, which ionizes the component molecules in the sample liquid. The ions generated are sent into the first intermediate vacuum chamber 14, which is in a low vacuum atmosphere, by way of a heating pipe 13. In the ionization chamber 11, other atmospheric ionization methods such as an atmospheric chemical ionization can be used other than the electrospray ionization method. Alternatively, such methods may be combined. Whatever the case may be, the ions are sent into the second intermediate vacuum chamber 17, which is in a medium vacuum atmosphere, via a small opening formed on top of a skimmer 16, while being converged by the first ion lens 15 arranged inside the first intermediate vacuum chamber 14. Then the ions are sent into the analysis chamber 19, which is in a high vacuum atmosphere, while being converged by an octapole-type second ion lens 18 arranged inside the second intermediate vacuum chamber 17.

In the analysis chamber 19, ions are once stored in a three-dimensional quadrupole ion trap 20 and, in some cases, may be mass-separated (mass-selected) and dissociated by a CID. Then the ions are exhausted collectively at a predetermined timing from the ion trap 20 to be introduced into a time-of-flight mass separator 21. Ions in the ion trap 20 are controlled with a voltage applied to each electrode (end cap electrode and ring electrode) from an IT (ion trap) power supply unit 28.

The time-of-flight mass separator 21 is a reflectron type, i.e. it includes a reflectron for reflecting ions with an electrostatic field. In the reflectron 22, ions are separated according to the mass (mass-to-charge ratio, to be exact) while they fly and return, which makes ions having smaller mass reach the ion detector 23 sooner. Ion detector 23 is composed of a combination of a conversion dynode for converting ions into electrons and a secondary electron multiplier for example, and provides an ion intensity signal according to the amount of ions which have reached the ion detector 23. The ion intensity signal is converted to digital values by an A/D converter (analog to digital converter) 24 and then provided to a data processor 25. The data processor 25 creates a mass spectrum, mass chromatogram, and total ion chromatogram. Based on such results, the data processor 25 performs a qualitative analysis, quantitative analysis, or other analyses. The data processor 25 includes a data memory 26 which stores and saves the data collected by the LC/MS.

To the controller 27 for controlling each unit in order to perform a mass analyzing operation as previously described, an operation unit 29, such as a keyboard and mouse, and a display unit 30, such as an LCD (liquid crystal display) are connected. The substance of the data processor 25 and the controller 27 is a personal computer. When the personal computer performs a dedicated control/processing program installed on the personal computer, the functions of the data processor 25 and the controller 27 are realized.

The mass spectrometer 10 can perform a normal MS, i.e. $MS^1$, analysis by simply storing and launching ions in the ion trap 20. The mass spectrometer 10 is also capable of performing an $MS^n$ analysis by repeating the selection of the ions' mass and dissociation of the ions by a collision induced dissociation process n-1 times in the ion trap 20. To perform the collision induced dissociation, a collision gas such as Ar gas is provided into the ion trap 20 from a gas supplier which is not illustrated. To store and dissociate ions, a linear ion trap or other means may be used other than a three-dimensional quadrupole ion trap. To perform the dissociation operation, an infrared multiphoton dissociation process or other process may be used other than a collision induced dissociation process.

Next, a characteristic analysis operation in the LC/MS according to the present embodiment will be explained with reference to FIGS. 2 through 4. FIG. 2 is a flowchart illustrating the process procedure of this characteristic analysis operation.

First, under the control of the controller 27, an $LC/MS^1$ analysis, i.e. an LC/MS analysis, in which a normal $MS^1$ analysis without a dissociation operation is carried out in the mass spectrometer 10, is performed using a predetermined sample to collect data (Step S1). Specifically, mass spectrum data in a predetermined mass range are repeatedly obtained as time progresses by repeating the following cycle: a predetermined sample is injected into a mobile phase by the injector 4 in the liquid chromatograph 1, and then in the mass spectrometer 10, various ions introduced into the ion trap 20 during a predetermined period of time are stored in the ion trap 20, and these ions stored are launched collectively at a predetermined timing to be introduced into the time-of-flight mass separator 21 to perform a mass analysis. Thus the data having three dimensions of a retention time, mass-to-charge ratio, and signal intensity can be collected. The data collected with regard to a certain sample is stored in the data memory 26 as one file.

The sample to be targeted in the $LC/MS^1$ analysis may be the sample to be analyzed. In this case, however, two sets of the samples for two LC/MS analyses are required. Hence, the sample to be targeted in the $LC/MS^1$ analysis may generally be a sample including components to be analyzed (e.g. a standard sample).

The data processor 25 creates a two-dimensional isointensity line graph based on the data, which is stored in the data memory 26, having three dimensions as previously described. In the isointensity line graph, a retention time is assigned to the horizontal axis, a mass-to-charge ratio is assigned to the longitudinal axis, and a signal intensity is represented in contour. The data processor 25 displays this graph on the screen of the display unit 30 via the controller 27 (Step S2). FIG. 3 illustrates an example of this isointensity line graph. The operator looks at this isointensity graph and specifies a range with regard to which an $MS^2$ analysis is to be performed by a drag operation with a mouse (or with another pointing device) or by a numerical input through a keyboard of the operation unit 29 (Step S3).

In the isointensity line graph, a series of peaks corresponding to a plurality of components having similar structures appears along the positive-slope line B in FIG. 3 for example. In the case where an $MS^2$ analysis focusing on a compound series including these plural compounds is required to be performed, the frame A can be specified with a drag operation or other operations so as to surround the peaks along the line B. To specify the range to be analyzed in the $MS^2$ analysis, other than such a graphical range specification operation, a function showing the relationship between a retention time and mass-to-charge ratio, or a margin value or the like to enlarge the width of the line (straight line or curving line) expressed with that function on a two-dimensional graph may be numerically provided through the keyboard of the operation unit 29 or selected by the mouse.

For example, in the case where the relationship between the retention time (RT) and the mass-to-charge ratio (m/z) shown by the line B is expressed by the following primary expression:

$$m/z = a \cdot RT + b, \text{ where } a \text{ and } b \text{ are proper constants,}$$

such a primary expression can be entered and Δ set as the margin value for m/z. With such an input, a belt-like frame A is set on the isointensity line graph as illustrated in FIG. 3.

When the range to be analyzed in an $MS^2$ analysis is specified as just described, the data processor 25 collects the data included in the range specified from the data memory 26 (Step S4). The data processor 25 subsequently extracts peaks included in the range and collects each peak's pertinent information, i.e. the mass-to-charge ratio and retention time. Regarding the retention time, not only a retention time in which a peak top appears but also a retention time width in which a signal intensity larger than a predetermined threshold value can be obtained is collected as the information (Step S5). Based on the information collected as just described, precursor ions are selected and assembled as a precursor ion list for example (Step S6). Ions corresponding to all the peaks existing in the range specified may be selected as precursor ions, or ions corresponding to the peaks within the range specified whose peak top is higher than a predetermined threshold value may be selected as precursor ions.

Next, the controller 27 creates, based on the precursor ion list, an $LC/MS^2$ execution schedule showing the relationship between the mass-to-charge ratio of the precursor ions to be analyzed as time progresses and the retention time (Step S7). The "$LC/MS^2$" in this specification specifically means the performance of an $MS^2$ analysis after a component separation in a liquid chromatograph. FIG. 4 illustrates an example of an $LC/MS^2$ execution schedule.

In the next step, the controller 27 performs an $LC/MS^2$ according to the $LC/MS^2$ execution schedule created as just described (Step S8). The schedule illustrated in FIG. 4 indicates that an $MS^2$ analysis is not performed during the retention time period of t0 through t1, and that during the retention time period of t1 through t2 which follows, an $MS^2$ analysis is performed with regard to two ions, which serve as precursor ions, whose mass-to-charge ratios are m1 and m2 respectively.

More specifically, in this $MS^2$ analysis, after various ions are introduced into the ion trap 20, a predetermined voltage is applied from the IT power supply unit 28 to the ring electrode or other components so that ions other than those having a mass-to-charge ratio of m1 are eliminated from the ion trap 20. After the selection of the precursor ion is performed in this manner, a collision gas is introduced into the ion trap 20 to dissociate the precursor ion to generate a variety of product ions. Subsequently, the product ions generated are launched collectively from the ion trap 20 to be introduced into the time-of-flight mass separator 21. Then a mass analysis is performed to obtain $MS^2$ spectrum data in the data processor 25. Next, $MS^2$ spectrum data for the precursor ion with a mass-to-charge ratio of m2 is also obtained in accordance with the same procedure. In this manner, $MS^2$ spectrum data for two kinds of precursor ions are repeatedly collected during the retention time t1 through t2. Since the product ion's signal intensity is generally low, it is preferable to collect data for the same precursor ion more than once and determine its summation in order to improve the $MS^2$ spectrum's S/N ratio.

During the next retention time period of t2 through t3, an $MS^2$ analysis is performed as previously described for ions with a mass m4 serving as a precursor ion to obtain the $MS^2$ spectrum data. During the next further retention time period of t3 through t4, an $MS^2$ analysis is performed in the same manner for three kinds of ions having masses m4, m5, and m6 serving as precursor ions to obtain the $MS^2$ spectrum data. It is preferable to repeatedly perform a normal $MS^1$ analysis after the point in time of the retention time 0, and perform an $MS^2$ analysis as well in addition to the $MS^1$ analysis only while a precursor ion is set in the schedule.

As previously described, in the LC/MS according to the present embodiment, it is possible to easily obtain the $MS^2$ spectrum of the ions corresponding to the peaks included in the range which the operator has specified on the isointensity line graph illustrated in FIG. 3. For example, as long as the range is appropriately set so that peaks corresponding to a plurality of compounds belonging to a compound series are included and unnecessary peaks other than those are included as few as possible, it is possible to assuredly obtain an $MS^2$ spectrum including the structural information of the compound to be targeted. Therefore, based on this, a structural analysis or other analyses can be easily performed.

In the aforementioned embodiment, precursor ions are selected based on the peaks contained in a specified range, e.g. the range surrounded by the frame A, on the isointensity line graph. Contrary to this, it is also possible to select precursor ions based on peaks other than those included in the range surrounded by the frame A. This method is useful in the case, for example, where a plurality of peaks of the compounds having a relatively large signal intensity interfere; such peaks are eliminated so that only a peak or peaks of the compound to be targeted can be studied.

Of course, the method for specifying a range at an intended position and with an intended size on an isointensity line graph is not limited to those described earlier. In addition, the number of ranges to be specified may not be only one but could be any number.

It should be noted that every embodiment described thus far is merely an embodiment of the present invention, and that any modification, adjustment, addition or the like properly made within the spirit of the present invention is also covered within the scope of the present invention. For example, although the present invention was applied to the LC/MS in the aforementioned embodiment, it can also be applied to a GC/MS. In addition, the mass spectrometer is not limited to the quadrupole type, but could be any type of mass spectrometer such as a time-of-flight type and an ion trap type.

What is claimed is:

1. A chromatograph mass spectrometer in which a chromatograph for separating a sample into components and a mass spectrometer for mass analyzing the sample components separated by the chromatograph are combined, and the mass spectrometer being capable of an $MS^n$ analysis in which an ion having a specific mass-to-charge ratio is selected as a precursor ion, the precursor ion selected is dissociated, and product ions created through the dissociation are mass analyzed, comprising:
   a) a graph displayer for creating a graph, based on data obtained by performing an $MS^1$ analysis, with a retention time and a mass-to-charge ratio as two axes on a plane, and with a signal intensity represented in contour or represented by an intensity-discriminable expression equivalent to the contour, and for displaying the graph on a display screen;
   b) a specifier for allowing a user to provide a visual indication on the graph displayed by the graph displayer, the visual indication specifying an intended range on the graph;
   c) a precursor ion selector for selecting one or more ions, as a precursor ion from the visual indication specifying the intended range, the one or more ions corresponding to a peak or peaks existing in the range specified by the specifier or a remaining peak or peaks other than the peak or peaks existing in the range; and
   d) an analysis controller for sequentially performing a series of predetermined $MS^2$ analyses, as time progresses, for the precursor ion or ions selected by the precursor ion selector.

2. The chromatograph mass spectrometer according to claim 1, wherein the graph is a two-dimensional contour graph drawn on a plane with the aforementioned two axes intersecting each other at right angles and contour lines representing the signal intensity.

3. The chromatograph mass spectrometer according to claim 1, wherein the specifier allows the user to set a frame having a predetermined form and size on the graph through a predetermined operation using a pointing device so that a range surrounded by the frame is specified as the aforementioned range.

4. The chromatograph mass spectrometer according to claim 1, wherein the specifier allows the user to enter an expression showing a relationship between the retention time and the mass-to-charge ratio.

5. The chromatograph mass spectrometer according to claim 4, wherein the specifier allows the user to enter a margin value expressing a deviation from the expression in order to provide a frame on the graph.

6. The chromatograph mass spectrometer according to claim 4, wherein the expression is a primary expression.

7. The chromatograph mass spectrometer according to claim 1, wherein the precursor ion selector selects a peak or peaks having larger signal intensity than a predetermined threshold value to determine a precursor ion.

* * * * *